(12) United States Patent
Baid (10) Patent No.: US 10,709,369 B2
(45) Date of Patent: Jul. 14, 2020

(54) NEEDLE ASSEMBLY WITH FLASHBACK CHAMBER FOR COLLECTING BLOOD OR OTHER LIQUID SAMPLES

(71) Applicant: POLY MEDICURE LIMITED, Kolkata (IN)

(72) Inventor: Rishi Baid, New Delhi (IN)

(73) Assignee: POLY MEDICURE LIMITED, Kolkata (IN)

( * ) Notice: Subject to any disclaimer, the term of this patent is extended or adjusted under 35 U.S.C. 154(b) by 365 days.

(21) Appl. No.: 15/021,264

(22) PCT Filed: Oct. 23, 2015

(86) PCT No.: PCT/IB2015/058178
§ 371 (c)(1),
(2) Date: Mar. 10, 2016

(87) PCT Pub. No.: WO2016/075574
PCT Pub. Date: May 19, 2016

(65) Prior Publication Data
US 2016/0278681 A1    Sep. 29, 2016

(30) Foreign Application Priority Data
Nov. 12, 2014   (IN) .......................... 1165/KOL/2014

(51) Int. Cl.
*A61B 5/15*  (2006.01)
*A61B 5/154*  (2006.01)
*A61M 25/06*  (2006.01)

(52) U.S. Cl.
CPC .... *A61B 5/150473* (2013.01); *A61B 5/15003* (2013.01); *A61B 5/1545* (2013.01);
(Continued)

(58) Field of Classification Search
CPC ........ A61M 25/0693; A61M 2005/311; A61M 25/0606; A61M 25/0097; A61B 5/150473; A61B 5/150496; A61B 5/1535
(Continued)

(56) References Cited

U.S. PATENT DOCUMENTS 4,416,290 A    11/1983  Lutkowski
7,615,033 B2 *  11/2009  Leong ............... A61B 5/150473
                                              600/573
2006/0009714 A1 *  1/2006  Higaki .................. F16K 15/021
                                              600/576

FOREIGN PATENT DOCUMENTS

EP    619096 A1    10/1994
EP    1796539 A1    6/2007
(Continued)

*Primary Examiner* — Charles A Marmor, II
*Assistant Examiner* — David Joseph Fernandez-Fidalgo
(74) *Attorney, Agent, or Firm* — Moore & Van Allen, PLLC; Henry B. Ward, III (57) ABSTRACT

A needle assembly comprising a housing, a first needle hub provided by the housing, a first hollow needle portion mounted to the first needle hub and extending from the first needle hub in a distal direction. A second needle hub is provided by the housing. A second hollow needle portion is mounted to the second needle hub and extends from the second needle hub in a proximal direction, opposite to the distal direction, wherein a hollow flashback chamber is arranged within the housing between the first needle portion and the second needle portion. The flashback chamber communicates with the inner lumen provided within the first and second hollow needle portion and is connected to the atmosphere by a passage and wherein a filter is provided within the passage, which is designed such that it is permeable for air to pour out of the flashback chamber into the atmosphere.

18 Claims, 5 Drawing Sheets

(52) U.S. Cl.
CPC .. *A61B 5/150213* (2013.01); *A61B 5/150389* (2013.01); *A61B 5/150572* (2013.01); *A61M 25/0693* (2013.01)

(58) Field of Classification Search
USPC ........................................................ 600/576
See application file for complete search history.

(56) References Cited

FOREIGN PATENT DOCUMENTS

| | | |
|---|---|---|
| EP | 2042089 A1 | 4/2009 |
| EP | 2097123 A1 | 9/2009 |
| EP | 2490592 A1 | 8/2012 |
| EP | 2670306 A1 | 12/2013 |
| EP | 2774539 A1 | 9/2014 |
| JP | 2002325749 A | 11/2002 |
| WO | 2006022716 A1 | 3/2006 |
| WO | 2012105968 A1 | 8/2012 |
| WO | 2016075574 A1 | 5/2016 |

\* cited by examiner

NEEDLE ASSEMBLY WITH FLASHBACK CHAMBER FOR COLLECTING BLOOD OR OTHER LIQUID SAMPLES

FIELD OF THE INVENTION

The present invention relates to a needle assembly for collecting blood or other liquid samples for discharge into a container, the needle assembly comprising a housing, a first needle hub provided by said housing, a first hollow needle portion mounted to said first needle hub and extending from said first needle hub in a distal direction, the first needle portion having a sharpened first needle tip, a second needle hub provided by said housing, and a second hollow needle portion mounted to said second needle hub and extending from said second needle hub in a proximal direction, opposite to said distal direction.

BACKGROUND OF THE INVENTION

Such needle assemblies, also known as blood collection needles are known in the art. The needle assembly is used e.g. by the medical practitioner in daily hospital routines. The first needle portion is placed within a patient's vein. Before or thereafter, a container having a rubber port is coupled with the second needle portion by sticking the second needle portion through the rubber port such that it protrudes into the hollow interior space of the container. In the following, the patient's blood can pour into the container. When the container is sufficiently filled with blood, it can be retracted from the second needle portion by the medical practitioner. Thereby, the rubber port sealingly closes again and the procedure can be repeated for receiving a further blood sample.

A critical step in the above described procedure is when the medical practitioner tries to place the first needle portion within the patient's vein. In particular in case of patients having a low blood pressure, as children, it can be difficult to locate the patient's vein. In those instances, it is advantageous to have a feedback indicating the medical practitioner if vein entry has been achieved. Such a feedback is usually called a flashback. When the vein entry is achieved, a particular portion of the needle assembly is filled by the patient's blood and thereby indicates to the medical practitioner the successful vein entry.

The European patent application EP 2 670 306 A1 shows a blood collection needle having a flashback feature. However, this prior art device has a complicated structure and is difficult and expensive to manufacture.

The European patent application EP 1 796 539 A1 shows another blood collection needle with a flashback feature. However, this device does not provide quick flashback indication, as is air included within the flashback chamber cannot pour out quickly enough.

The European patent application EP 2 097 123 A1 shows a further blood collection needle with a flashback feature. A punctured needle extends through a housing surrounding the needle in the punctured section. The housing provides a flashback chamber. A filter is arranged in one of the housings outer walls. However, this device has the drawback that the flashback chamber is formed by a large lumen such that undesired large amount of patient's blood is collected for flashback purposes. The same drawback applies for the prior art documents according to the European patent applications EP 2 042 089 A1 and EP 2 490 592 A1.

OBJECT OF THE INVENTION

It is the object of the present invention to provide a needle assembly for collecting blood or other liquid samples for discharge into a container as described above, which is easy and cost-efficient to manufacture and which provides a quick flashback requiring only little amounts of the patient's blood.

SUMMARY OF THE INVENTION

This object is achieved by a needle assembly for collecting blood or other liquid samples for discharge into a container, the needle assembly comprising a housing, a first needle hub provided by said housing, a first hollow needle portion mounted to said first needle hub and extending from said first needle hub in a distal direction, the first needle portion having a sharpened first needle tip, a second needle hub provided by said housing, and a second hollow needle portion mounted to said second needle hub and extending from said second needle hub in a proximal direction, opposite to said distal direction. In the needle assembly, a hollow flashback chamber is arranged within the housing between the first needle portion and the second needle portion, wherein the flashback chamber communicates with the inner lumen provided within the first and second hollow needle portion, wherein the housing is formed from transparent material at least in a region close to the flashback chamber, wherein the flashback chamber is connected to the atmosphere by a passage, and wherein a filter is provided within the passage, wherein the filter is designed such that it is permeable for air to pour out of the flashback chamber into the atmosphere but prevents blood or other liquid samples contained in the flashback chamber from pouring out through an opening into the atmosphere.

According to the invention, the flashback chamber directly communicates with the atmosphere via the filter. When the needle assembly is positioned within the patient's vein such that the needle tip of the first needle portion enters into the patient's vein, blood can pour into the inner lumen of the first needle portion and flow through the hollow first needle portion into the flashback chamber. The air contained within the inner lumen of the first needle portion and within the flashback chamber can easily flow out into the atmosphere via the passage and through the filter. Thereby, the flashback is not delayed through a counter-pressure provided by air contained within the inner lumen of the first needle portion and within the flashback chamber. This air can emit quickly enough from the inner lumen of the first needle portion and the flashback chamber through the filter. Thereby, the medical practitioner is provided with a quick flashback indication. As soon as the blood comes into contact with the filter material, the filter material seals the flashback chamber and prevents any leakage of blood into the surroundings. As the flashback chamber is arranged in a small region between the first and the second needle portion, it has a small lumen and does not require a large amount of the patient's blood. The needle assembly according to the invention has a simple structure and is therefore easy to manufacture.

According to one embodiment of the invention, the whole housing is formed from transparent material, in particular from transparent plastics.

According to another embodiment of the invention, the flashback chamber has a distal entry diameter equal to or smaller than an inner diameter of the hollow first needle portion. Having an equal diameter ensures a constant flow of blood through the needle assembly and at the same time reduces the amount of blood for a quick flashback indication. Having a smaller diameter increases the flow speed of the blood within the flashback chamber such that a quicker flashback indication can be provided.

According to a further embodiment of the invention, the housing includes an outer shell, a distal body and an inner tubular portion, wherein the outer shell surrounds a hollow space, wherein the outer shell is connected to the inner tubular portion by the distal body. Furthermore, the invention may provide that the first needle hub is formed at least partially by the distal body.

In order to provide a small flashback chamber and in order to avoid a loss of an excessively large amount of patient's blood for flashback purposes, the flashback chamber can be arranged at least partially within the inner tubular portion.

In regard to the structure of the needle assembly, it is possible according to the invention that the first needle portion is formed by a first needle and that the second needle portion is formed by a second needle, wherein the first needle is formed separately from the second needle, wherein facing needle ends limit the flashback chamber and wherein the port opens into the flashback chamber between the facing needle ends of the first and second needle portions.

In order to facilitate manufacturing of the needle assembly and at the same time reliably set the longitudinal extension of the flashback chamber, the flashback chamber is defined by a diameter reduced portion of an axial inner through hole of the inner tubular portion of the distal body, thereby serving as an abutment to the first and second needle, when the needles are plugged into the respective needle receiving portions of the needle assembly during assembly.

Advantageously, the longitudinal extension of the flashback chamber substantially equals an inner diameter of an entry opening of the passage from the flashback chamber, i.e. an inner diameter of a cylindrical channel. This measure further reduces the size of the flashback chamber and the amount of blood necessary for a flashback indication.

It is further advantageous that the first needle is fixedly held only in the housing and the second needle is fixedly held only in a separate plug member. Hence, the housing and the plug member, which form a sealing connection, may be individually pre-assembled with the respective needle for an easier manufacturing of the needle assembly and mounted to one another after re-assembly.

Having a cylindrical filter with a larger diameter on its atmosphere side than an inner diameter of an entry opening of the passage from the flashback chamber is further advantageous, because a certain blockage of the filter from the atmosphere side, e.g. by pollution, is compensated by the diameter difference, such that throughput of air through the filter and to the atmosphere is still ensured.

Another advantage of the invention provides the optional feature that the filter further is arranged between an interior space and the atmosphere. This ensures that, for example, during the manufacturing of the needle assembly, in which the housing and a plug member are sealingly connected, air can escape from within the interior space and into the atmosphere, thus eliminating a constant internal pressure in the needle assembly.

Advantageously, the flashback chamber is visible from the outside of the housing through at least two transparent material layers with a layer of fluid there between, the fluid preferably being air. Thereby an optical magnification of the flashback chamber can be achieved by proper selection of the material/fluid and the layer thickness, for example, which helps ensure that the medical practitioner quickly and reliably recognizes a successful vein entry.

As an alternative to the structure described above, it is possible that the first needle portion and the second needle portion are formed by a single needle extending through the housing, wherein the needle has an opening arranged within or close to the flashback chamber. In this case, the opening in the needle can be directed to the passage provided in the housing.

Moreover, the invention may provide that the housing is formed with a connecting portion for coupling the needle assembly to a container holder. In this regard, it is possible that the second needle hub is formed at least partially by the connecting portion. According to one embodiment, the connecting portion has an outer thread adapted to be screwed into a corresponding inner thread provided on the container holder. The invention may further provide that the second needle portion is sealingly received within the connecting portion. Moreover, it is possible according to the invention that the connecting portion is formed by a plug member sealingly received within the housing.

In order to seal the second needle such that blood does not immediately pour out of the second needle after the first needle has been placed within the patient's vein, it can be provided that the second needle is covered by a flexible sealing sleeve.

The invention may further provide that the first needle portion is sealingly received within the distal body of the housing.

According to the invention, it is possible that the filter is formed by a hydrophobic or hydrophilic material.

BRIEF DESCRIPTION OF THE ACCOMPANYING DRAWINGS

In the following, a specific embodiment of the present invention is described based on the accompanying figures. It is shown in.

DETAILED DESCRIPTION OF THE INVENTION

Figure 1:
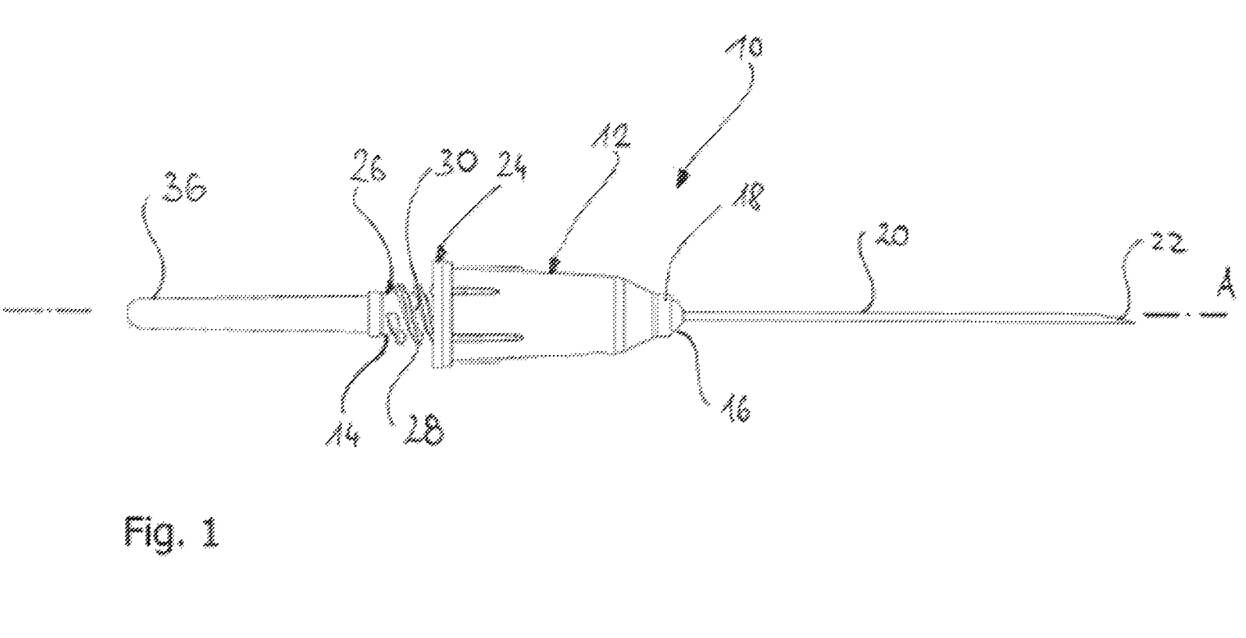
FIG. 1 a side view of the needle assembly according to the present invention.
Figure 2:
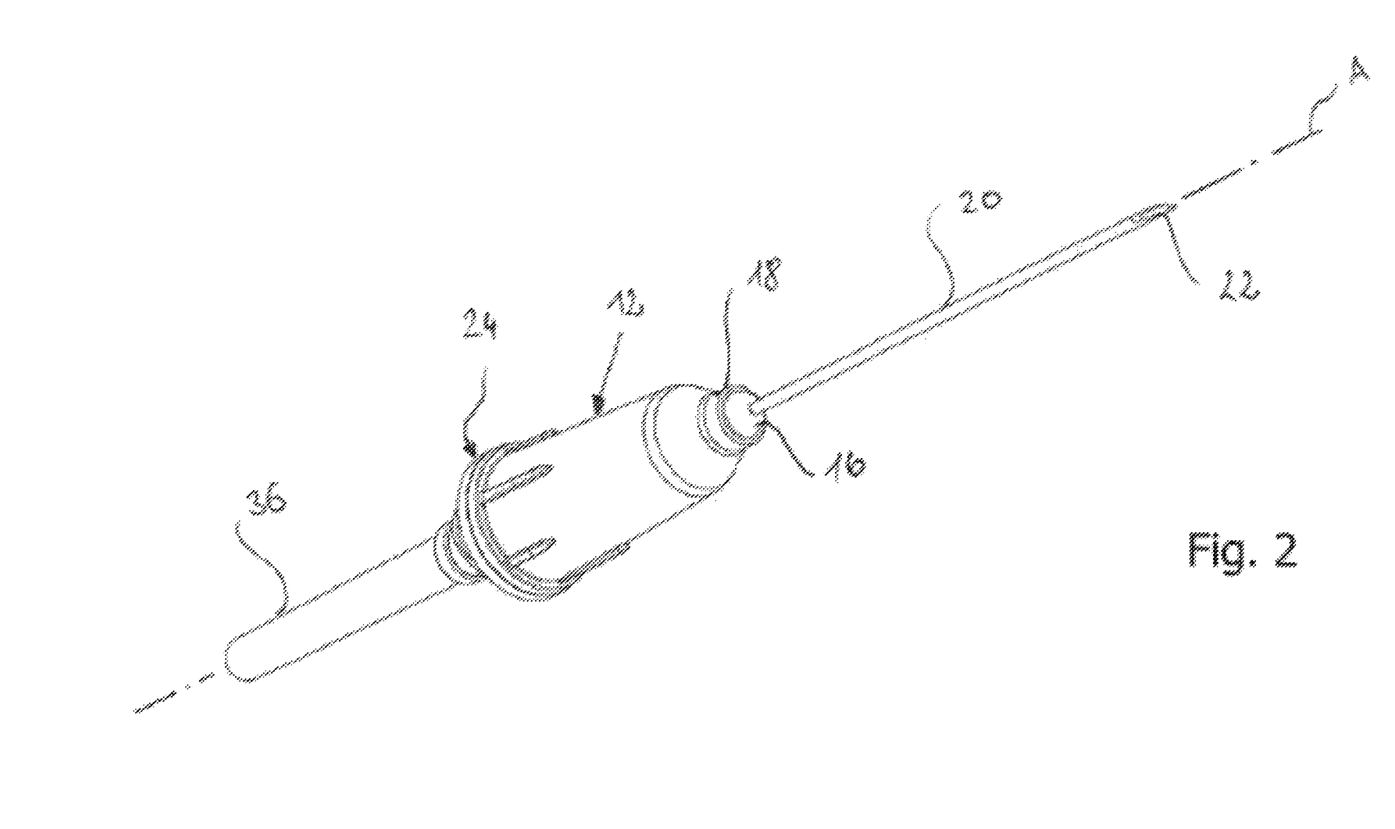
FIG. 2 a perspective view of the needle assembly according to the present invention.

In FIG. 1 a side view and in FIG. 2 a perspective view of a needle assembly 10 according to the present invention are shown. The needle assembly 10 is provided for collecting blood or other liquid samples for discharge into a liquid collection container (not shown). The needle assembly 10 comprises a housing 12. The housing 12 is formed from transparent plastic material. The needle assembly 10 has a proximal end 14 and a distal end 16. The housing 12 is provided with a first needle hub 18. The first needle hub receives a first hollow needle 20 mounted to said first needle hub 18 and extending from said first needle hub 18 in a distal direction along a longitudinal axis A. The first needle has a sharpened first needle tip 22, which is provided with a particular sharpening pattern such that it can easily penetrate a patient's skin and enter into a patient's vein.

The needle assembly 10 is provided on its proximal end 14 with a proximal plug member 24, that is fixedly and sealingly received within the housing 12. The plug member 24 is integrally formed with a cylindrical portion 26. An outer thread 28 is provided on the outer circumferential surface of the cylindrical portion 26. The plug member 24 forms a second needle hub 30 receiving a second needle 32.

Figure 3:
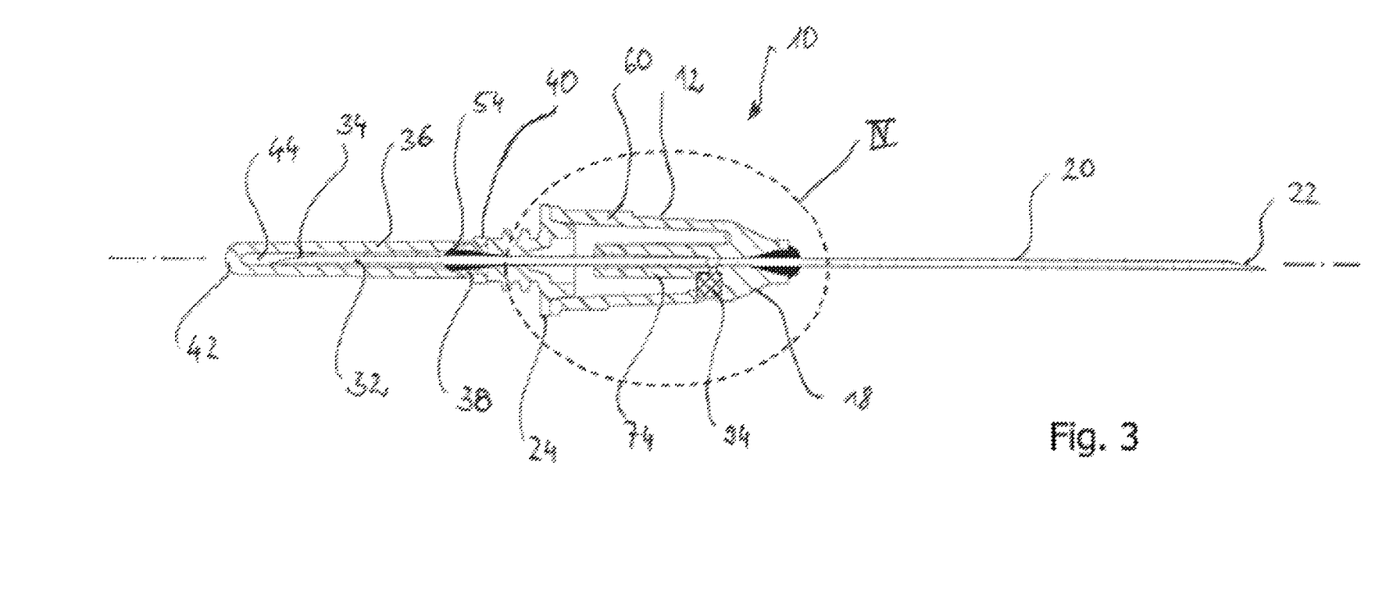
FIG. 3 a longitudinal sectional view of the needle assembly according to the present invention.

Reference is also made to FIG. 3, showing a longitudinal section of the needle assembly 10. The second needle 32 is mounted to said second needle hub 30 and extends from said second needle hub 30 in a proximal direction along the longitudinal axis A, opposite to said distal direction. As can be seen in FIG. 3, the second needle 32 also has at its proximal end 34 a sharpened needle tip. The second needle 32 is surrounded by a flexible sleeve 36, which is fixedly and sealingly attached to a fixing portion 38 integrally formed on the cylindrical portion 26 of the proximal plug member 24. In order to provide a sufficiently high attachment force, the flexible sleeve 36 is provided at its distal end with a thickened mounting ring 40.

At its proximal end 42 the flexible sleeve 36 is closed in rounded shape. It is to be noted that the axial length of the flexible sleeve 36 is chosen such that in the ready state as shown in FIG. 3 there is a gap 44 between the needle tip 34 and the proximal end 42 of the flexible sleeve 36.

Figure 4:
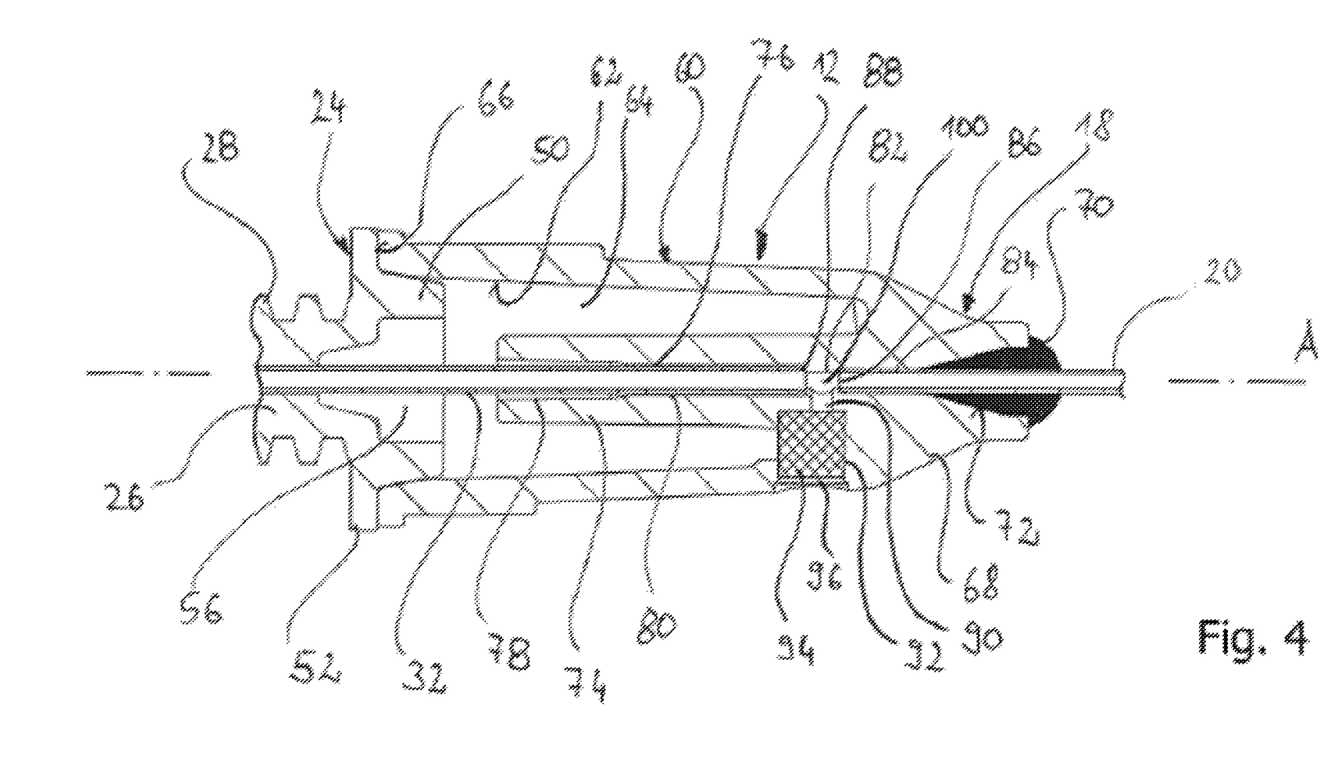
FIG. 4 an enlarged view of the portion IV surrounded in FIG. 3 by the interrupted line.

Referring now to the needle assembly 10 and its components, it is additionally referred to the enlarged section shown in FIG. 4. The proximal plug member 24 is provided with a conical protrusion 50 protruding in axial distal direction from a flange 52 integrally formed on the cylindrical portion 26. The cylindrical portion 26 tightly and fixedly holds the second needle 32. Additional sealing material 54 is provided in order to hold and seal the second needle 32 within the proximal plug member 24. An inner recess 56 within the proximal plug member 24 facilitates manufacturing, in particular introducing the second needle 32 during the manufacturing process.

The housing 12 includes an outer shell 60 having a stepped outer circumferential surface and surrounding by its inner circumferential surface 62 an interior space 64. The inner circumferential surface 62 conically opens in proximal direction and is dimensioned such that it sealingly receives the conical protrusion 50 of the proximal plug member 24. In the assembled and sealed condition, as shown, the conical protrusion 50 sealingly engages the proximal portion of the inner circumferential surface 62 of the outer shell 60. The flange 52 abuts against an end surface 66 of the outer shell 60.

The outer shell 60 is integrally formed with a substantially conical distal body 68 at the proximal end of the housing 10. The conical distal body 68 provides the first needle hub 18. The first needle 20 is fixedly and sealingly received within said first needle hub 18. Additionally, a sealing material 70 is arranged in a conical recess 72 at the distal and of the distal body 68 in order to hold and seal the first needle 20.

The distal body 68 is integrally formed with an inner tubular portion 74 extending axially in proximal direction into the interior space 64 surrounded by the outer shell 60. However, the axial length of the inner tubular portion 74 is substantially shorter than the axial length of the outer shell 60 such that a non-demanded contact between the proximal plug member 24 and a proximal end of the inner tubular portion 74 during the assembly can be excluded.

The inner tubular portion 74 and the distal body 68 have an axial inner through hole 76, with a widened proximal end 78 facilitating the introduction of the distal and of the second needle 32 when assembling. The widened proximal end 78 leads into a cylindrical portion 80 of the through hole 76 tightly receiving a distal end portion of the second needle 32. The through hole 76 has a short flashback chamber portion 82 with a slightly reduced diameter. Next to the flashback chamber portion 82 in distal direction, the through hole 76 has a cylindrical portion 84 tightly receiving the proximal end of the first needle 20. The cylindrical portion 84 leads into the conical recess 72.

According to the above, the interior space 64 becomes a space enclosed by the housing 12 and the plug member 24.

Figure 5:
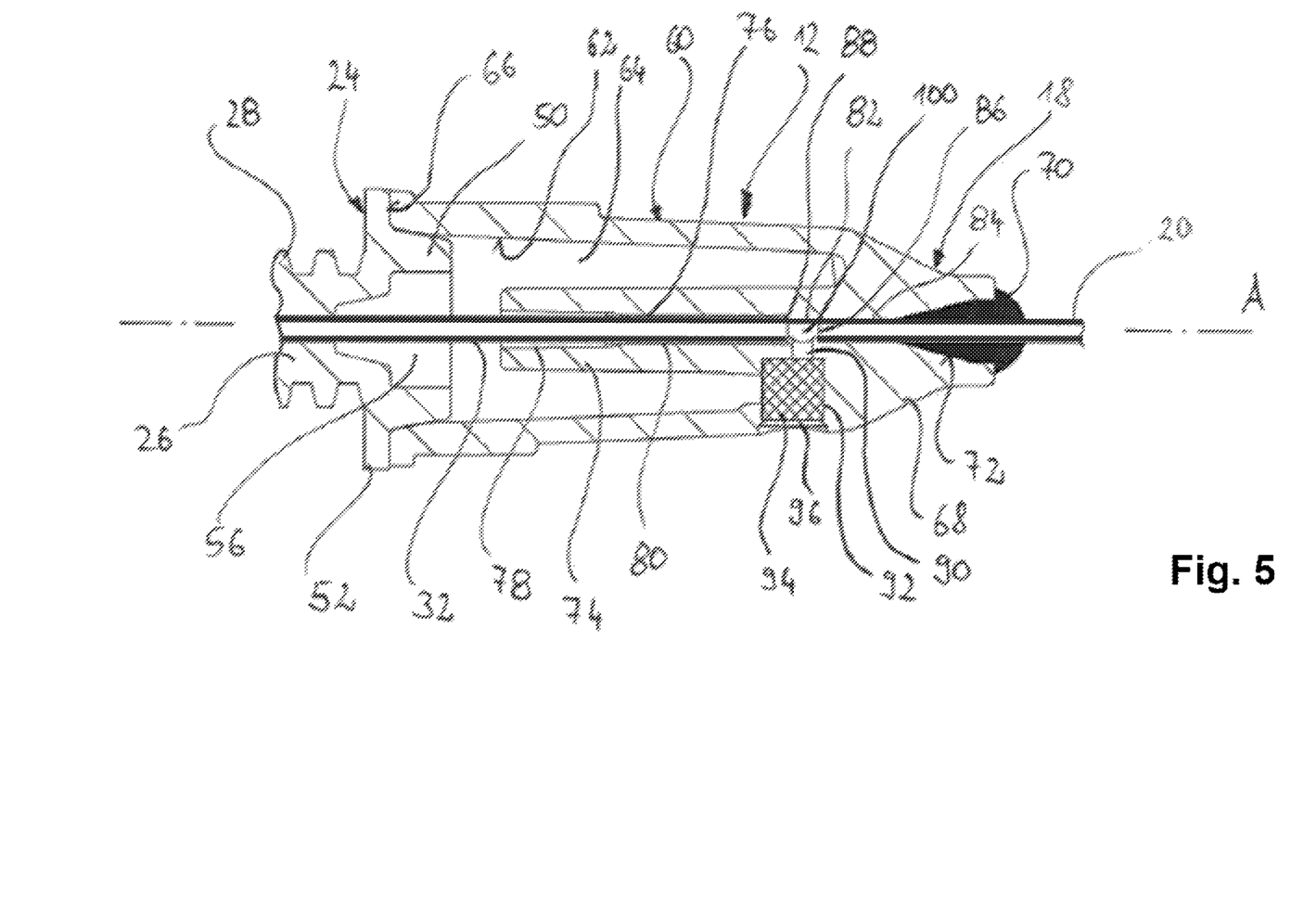
FIG. 5 an enlarged view of the portion IV surrounded in FIG. 3 by the interrupted line in accordance with another embodiment of the invention.

As can be seen in FIGS. 3 and 4, the proximal end 86 of the first needle 20 and the distal end 88 of the second needle 32 are arranged opposite to one another in a distance provided by the flashback chamber portion 82. In another embodiment of the invention, as illustrated in FIG. 5, the first needle 20 and the second needle 32 are formed by a single needle extending through the housing, wherein the needle has an opening arranged within or close to the flashback chamber portion 82. A cylindrical channel 90 extending transversely from the flashback chamber portion 82 to the axial direction A is arranged within the housing 12. The cylindrical channel 90 leads into a recess 92. The recess 92 is open to the atmosphere by a lateral opening 96 formed in the outer circumferential surface of the housing 12. The recess 92 receives a cylindrical filter 94, which is tightly arranged within the recess 92. The filter 94 is formed from hydrophobic material, i.e. material repelling water and other liquids. However, the filter material allows the passage of air.

The cylindrical channel 90, the recess 92 and the lateral opening 96 are also referred to as a passage, which connects the flashback chamber portion 82 to the atmosphere.

In use, the needle assembly 10 according to the described embodiment is provided with a known container holder (not shown) that is screwed onto the cylindrical portion 26 in a conventional way. A conventional blood collection container (not shown) can be plugged onto the second needle 32. A medical practitioner places the distal portion of the first needle 20 in a patient's vein. As soon as the sharpened needle tip 22 has entered the patient's vein, blood pours into the hollow interior of the needle 22 in axial direction. The air contained within the hollow interior of the needle 22 is pressed out of the needle and can pour through the filter 94 into the atmosphere. Thereby, a fast evacuation of air can be achieved avoiding counter-pressure onto the blood flow, even in case of a patient having low blood pressure. Thus, the patient's blood quickly enters into the hollow lumen within the flashback chamber portion 82 forming a flashback chamber 100. The blood entering the flashback chamber 100 can be easily and quickly seen by the medical practitioner and provides rapid indication on a successful vein entry. As soon as the blood comes into contact with the hydrophobic material of the filter 94, the filter material seals the flashback chamber 100 and the cylindrical channel 90 in order to avoid any blood leakage.

The patient's blood further flows into the second needle 32. However, the flexible sleeve 36 prevents leakage of blood in case no blood collection container is arranged on the second needle 32. Moreover, the flexible sleeve 36 elastically expands into the form shown in FIG. 3 as soon as a blood collection container filled with a blood sample is removed until it is occasionally replaced by another blood collection container for taking a further blood sample.

The present invention is beneficial as it provides a quick flashback in a very distal portion of the housing 12. The filter 94 allows a quick evacuation of air contained within the flashback chamber 100 and the inner lumen of the hollow first needle 20. This is particularly beneficial in case of taking a blood sample of a patient having a low blood pressure. Thereby, the time period until the flashback appears to the medical practitioner after the needle tip 22 has entered the patient's vein can be substantially reduced. Despite the quick and reliable indication of successful vein entry as described above, the amount of blood necessary for achieving the flashback is very little. The needle assembly 10 according to the present invention has a simple structure and is easy to manufacture. It leads to lower manufacturing costs.

Although this invention has been disclosed in the context of certain preferred embodiments and examples, it will be understood by those skilled in the art that the present invention can be constructed and utilized in a plethora of different ways. It should be understood that many changes, modifications, variations and other uses and applications will become apparent to those persons skilled in this particular area of technology and to others after having been exposed to the present specification and accompanying drawings. Any and all such change, modifications, variations, and other uses and applications which do not depart from the spirit and scope of the present invention are therefore covered by and embraced within the present invention and the claims set forth herein-below.

The invention claimed is:

1. A needle assembly for collecting blood or other liquid samples for discharge into a container, the needle assembly comprising:
   a housing;
   a first needle hub provided by said housing;
   a first hollow needle portion mounted to said first needle hub and extending from said first needle hub in a distal direction;
   a second needle hub provided by said housing;
   a second hollow needle portion mounted to said second needle hub and extending from said second needle hub in a proximal direction, opposite to said distal direction;
   wherein a hollow flashback chamber is arranged within the housing and extends longitudinally from a proximal end of the first needle portion to a distal end of the second needle portion, wherein the flashback chamber communicates with an inner lumen provided within the first and second hollow needle portion, wherein the housing is formed from transparent material at least in a region close to the flashback chamber, wherein the flashback chamber is connected to the atmosphere by a passage and wherein a filter is provided within the passage, wherein the filter is configured to be permeable for air to pour out of the flashback chamber into the atmosphere but prevents blood or other liquid samples contained in the flashback chamber from pouring out through an opening into the atmosphere; and
   wherein a longitudinal length of the flashback chamber approximately equals an inner diameter of an entry opening of a cylindrical channel of the passage extending transversely from a longitudinal axis of the flashback chamber.

2. The assembly according to claim 1, wherein the housing is formed from transparent plastics.

3. The assembly according to claim 1, wherein the housing includes an outer shell, a distal body and an inner tubular portion, wherein the outer shell surrounds a hollow space, wherein the outer shell is connected to the inner tubular portion by the distal body.

4. The assembly according to claim 3, wherein the flashback chamber is arranged at least partially within the inner tubular portion.

5. The assembly according to claim 1, wherein the first needle hub is formed at least partially by a distal body.

6. The assembly according to claim 1, wherein the first needle portion is formed by a first needle and wherein the second needle portion is formed by a second needle, wherein the first needle is formed separately from the second needle, wherein the first needle comprises an end and the second needle comprises an end and the ends of the first and second needle are facing one another so as to define facing needle ends, wherein facing needle ends limit the flashback chamber and wherein a port opens into the flashback chamber between the facing needle ends of the first and second needle portions.

7. The assembly according to claim 1, wherein the first needle portion and the second needle portion are formed by a single needle extending through the housing, wherein the needle has an opening arranged within or close to the flashback chamber.

8. The assembly according to claim 7, wherein the opening in the needle is directed to the passage provided in the housing.

9. The assembly according to claim 1, wherein the housing is provided with a threaded connecting portion for coupling the needle assembly to a container holder.

10. The assembly according to claim 9, wherein the second needle hub is formed at least partially by the threaded connecting portion.

11. The assembly according to claim 9, wherein the threaded connecting portion has an outer thread adapted to be screwed into a corresponding inner thread provided on the container holder.

12. The assembly according to claim 9, wherein the second needle portion is sealingly received within the threaded connecting portion.

13. The assembly according to 9, wherein the threaded connecting portion is formed by a plug member sealingly received within the housing.

14. The assembly according to claim 1, wherein the first needle portion is sealingly received in a distal body of the housing.

15. The assembly according to claim 1, wherein the filter is formed by a hydrophobic or hydrophilic material.

16. The assembly according to claim 1, wherein the filter is cylindrical and with a larger diameter on its atmosphere side than an inner diameter of an entry opening of the passage from the flashback chamber.

17. The assembly according to claim 1, wherein the filter is arranged between an interior space and the atmosphere.

18. The assembly according to claim 1, wherein the flashback chamber is visible from the outside of the housing through at least two transparent material layers with a layer of fluid there between.

* * * * *